United States Patent [19]

Jensen

[11] Patent Number: 4,723,944
[45] Date of Patent: Feb. 9, 1988

[54] FLUID COLLECTION RECEPTACLE WITH IMPROVED NON-RETURN VALVE

[76] Inventor: Ole R. Jensen, 646 Orangeburg Rd., River Vale, N.J. 07675

[21] Appl. No.: 870,788

[22] Filed: Jun. 5, 1986

[51] Int. Cl.⁴ .............................................. A61M 1/00
[52] U.S. Cl. ..................................... 604/323; 383/44; 383/51
[58] Field of Search .................. 128/760, 767; 383/44, 383/51, 57; 604/323, 335, 350

[56] References Cited

U.S. PATENT DOCUMENTS

| | | | |
|---|---|---|---|
| 2,640,484 | 6/1953 | Johnson | 383/44 |
| 3,282,412 | 11/1966 | Corella, Jr. et al. | 383/44 |
| 4,300,560 | 11/1981 | Steer | 128/283 |
| 4,391,404 | 7/1983 | Welter | 383/51 |
| 4,421,509 | 12/1983 | Schneider et al. | 604/317 |
| 4,462,510 | 7/1984 | Steer et al. | 604/248 |
| 4,533,354 | 8/1985 | Jensen | 604/323 |
| 4,604,095 | 8/1986 | Samuelson | 604/323 |

FOREIGN PATENT DOCUMENTS 863295 3/1961 United Kingdom .
1139715 1/1969 United Kingdom .

Primary Examiner—John D. Yasko
Assistant Examiner—J. L. Kruter
Attorney, Agent, or Firm—James & Franklin

[57] ABSTRACT

A urine collection receptacle has a body formed by walls sealed along the periphery. First and second sheets form a drape which is situated between the walls. The drape extends across the body below the inlet, with the side edges of the drape sealed along opposing sections of the periphery. The sheets are sealed to each other along spaced vertical lines to define the body of a flap valve. The vertical sealed lines are severed to detach the flap valve body from the remainder of the drape. The sheets may also be sealed along oppositely oriented, downwardly inclined lines to form a funnel to direct liquid from the inlet toward the flap valve. The structure facilitates manufacture because the drape is sealed to the receptacle body in the same automated operation which seals the periphery of the walls.

3 Claims, 11 Drawing Figures

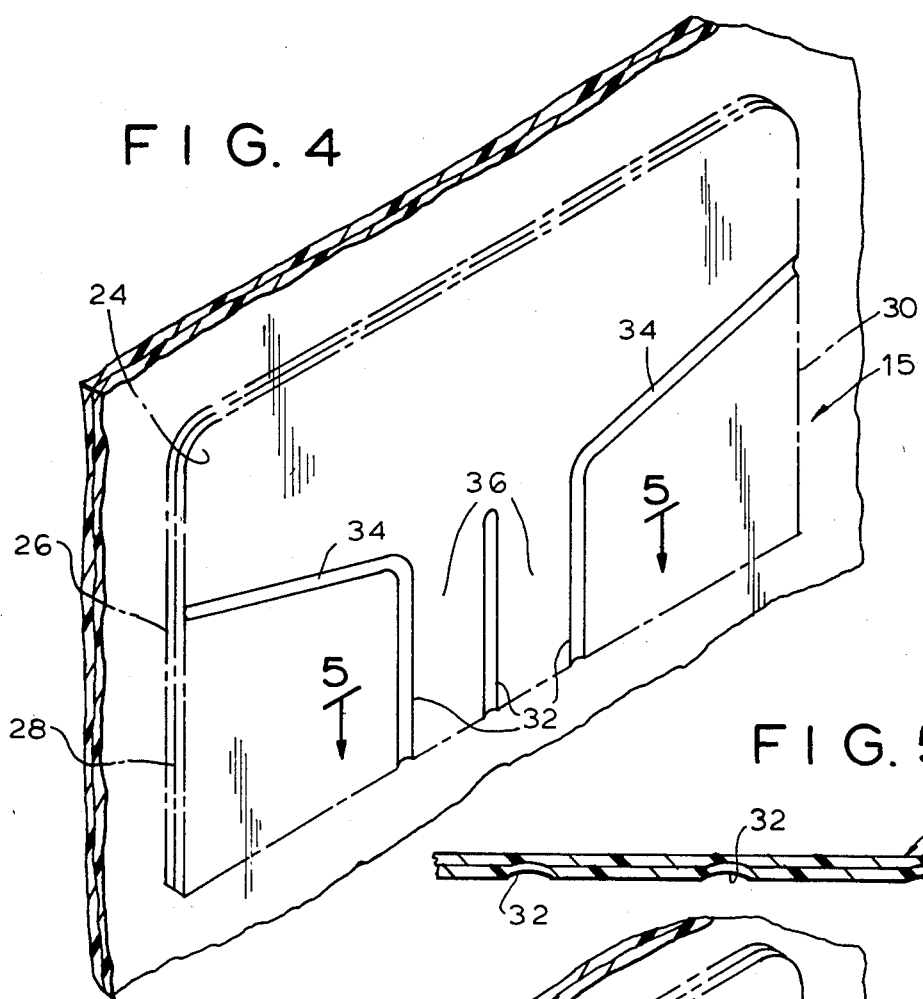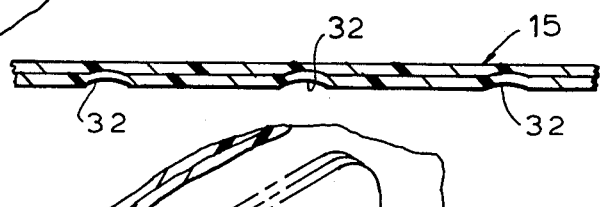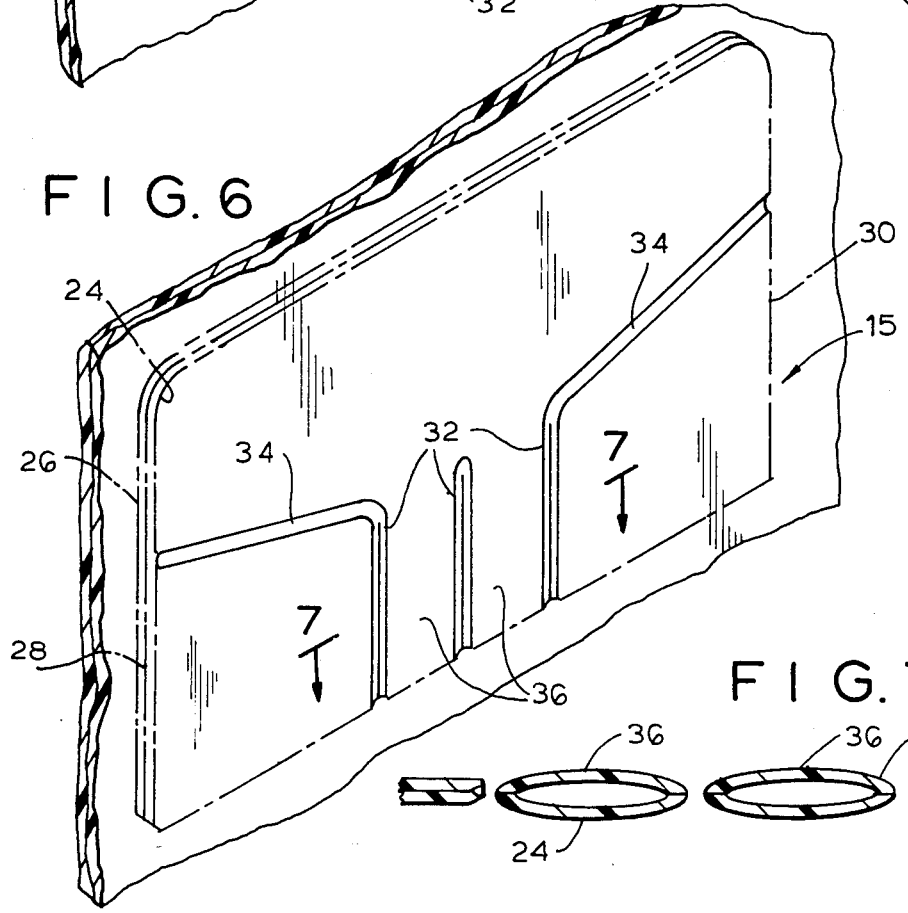

FLUID COLLECTION RECEPTACLE WITH IMPROVED NON-RETURN VALVE

The present invention relates to non-return valves for use in fluid collection receptacles such as those designed for medical purposes and, more particularly, to an improved non-return valve with simplified structure and the method of manufacturing same.

In a variety of medical situations, it is necessary to provide a body fluid collection receptacle, such as a drainage pouch or bag, which may be worn by a mobile patient, for example, by being strapped to the patient's leg or abdomen. Such receptacles may be useful for collecting urine from individuals who are incontinent. Internal or external catheters are utilized which are connected to a leg mounted fluid collection receptacle by means of a flexible tube. Individuals having undergone abdominal surgical procedures such as ureterostomies may have waste material discharged from the body through a stoma in an uncontrollable manner. Collection receptacles are detachably mounted to the body of such individuals so as to collect such waste materials.

Fluid collection receptacles used for the above purposes, because they are designed to be mounted on the body of a mobile patient, have an inherent problem involving the back-flow of liquid as the patient moves. Such back-flow is highly undesirable as it may create an unsanitary condition or cause discomfort resulting from skin irritation and infection.

In order to overcome this problem, fluid collection receptacles of the type here under discussion are commonly provided with non-return valves, often in the form of flap valves. Flap valves can be fabricated in a number of different configurations, but are normally attached to the inlet tube which extends into the receptacle or to the walls of the receptable itself. Accordingly, the manufacturing process, which for the basic receptacle is relatively simple, becomes much more complex and, hence, costly, in some cases requiring a hand operation to properly form and insert the non-return valve.

In general, the present invention relates to an improved non-return valve designed for use in a fluid collection receptacle adapted for medical applications and a method of manufacturing same in which one or more flap valves are formed in with a simplified structure. The structure permits optimum operation of the valves and, at the same time, significantly simplifies the manufacturing process which can now be completely automated.

In general, these objects are achieved by forming the non-return valve out of a drape consisting of face-to-face sheets of flexible plastic material. The sheets are sealed together along sets of spaced vertical lines which define the body of one or more flap valves and inclined lines which form a funnel. The valve bodies are detached from the remainder of the drape by severing along the sealed lines. The drape is sealed into the receptacle during the same operation which seals the periphery of the walls. Because of the simplicity of the structure and the method of mounting the drape, the entire process can be performed in a highly automated manner, thereby greatly reducing the cost of the product while at the same time increasing its effectiveness.

It is, therefore, a prime object of the present invention to provide an improved non-return valve and method for manufacturing same including a drape consisting of first and second sheets attached to the receptacle walls along the sealed periphery thereof.

It is another object of the present invention to provide an improved non-return valve and method of manufacturing same wherein the sheets which form the drape are sealed together along sets of spaced lines which define the bodies of one or more flap valves.

It is another object of the present invention to provide an improved non-return valve and method for manufacturing same wherein the sealed lines are severed as as to detach the body of the flap valve from the remainder of the drape.

It is another object of the present invention to provide an improved non-return valve and method for manufacturing same wherein a funnel-like structure is created so as to direct fluid into the flap valve by simply sealing the sheets along oppositely inclined lines extending from the side edges of the sheets towards the flap valve.

It is another object of the present invention to provide an improved non-return valve and method for manufacturing same wherein a simplified and automated process can be utilized to manufacture the receptacle.

In accordance with one aspect of the present invention, a non-return valve assembly is provided for use in a fluid collection receptacle of the type having a body formed by walls sealed along the periphery. The assembly includes a drape comprising first and second plastic sheets. The drape is situated between the walls and has a section extending across the body. Substantially the entire side edges of the drape section are sealed along opposing portions of the periphery. The sheets are sealed to each other along spaced lines extending generally in the same direction within the section to define the body of the flap valve means. The drape is severed along the sealed lines to substantially detach the valve body from the remainder of the section.

The sheets are further sealed along oppositely inclined lines extending from the side edges of the drape towards the spaced sealed lines. In this manner, a funnel-like section is defined above the flap valve means.

The spaced sealed lines are preferably generally parallel to each other. In addition, sets of spaced lines sealed and severed to define the body of more than one flap valve means may be provided.

In accordance with another object of the present invention, a fluid collection receptacle is provided including an inlet, a body defined by walls sealed along the periphery and non-return valve means. The valve means comprises a drape including first and second sheets situated between the walls. The drape has a section extending substantially across the body with substantially the entire side edges of the section being sealed between opposing portions of the periphery. The sheets are sealed to each other along spaced lines extending generally in the same direction within the section to define the body of flap valve means. The drape is severed along the sealed lines to substantially detach the valve body from the ramainder of the drape.

In accordance with another aspect of the present invention, a method is provided for manufacturing a fluid collection receptacle of the type having a body elongated in a given direction. The method includes the steps of forming a drape by placing first and second sheets in face-to-face relation. The sheets are sealed together along spaced lines extending in the same general direction, within a section of the sheets, to form the body of flap valve means. The drape is then severed along the sealed lines to substantially detach the body of the flap means from the remainder of the drape. Thereafter, the drape is placed between the walls of the receptacle. The walls are substantially longer than the drape along the given (vertical) direction and align with the side edges of the section. The periphery of the walls is sealed with substantially the entire side edges of the section therebetween such that the section extends substantially across the body.

The process further comprises the step of sealing the sheets along oppositely inclined lines extending from the side edges of the section towards the flap valve means body. In this manner, a funnel-like section between the inlet and the flap valve means is formed.

The process of the present invention further comprises the steps of sealing the sheets along sets of spaced lines and severing the sealed lines to define the bodies of more than one flap valve means. In this manner, multiple flap valve means can be formed without any additional process steps.

To these and to such other objects which may hereinafter appear, the present invention relates to an improved non-return valve and method of manufacturing same, as set forth in the following specification and recited in the annexed claims, taken together with the accompanying drawings, wherein the numerals refer to like parts and in which:

FIG. 4 is an isometric view of the drape of the present invention after the sealing operation;

FIG. 5 is a cross-sectional view of the drape of the present invention taken along line 5—5 of FIG. 4;

FIG. 6 is an isometric view of the drape of the present invention after the severing operation;

FIG. 7 is a cross-sectional view taken along line 7—7 of FIG. 6;

Figure 1:
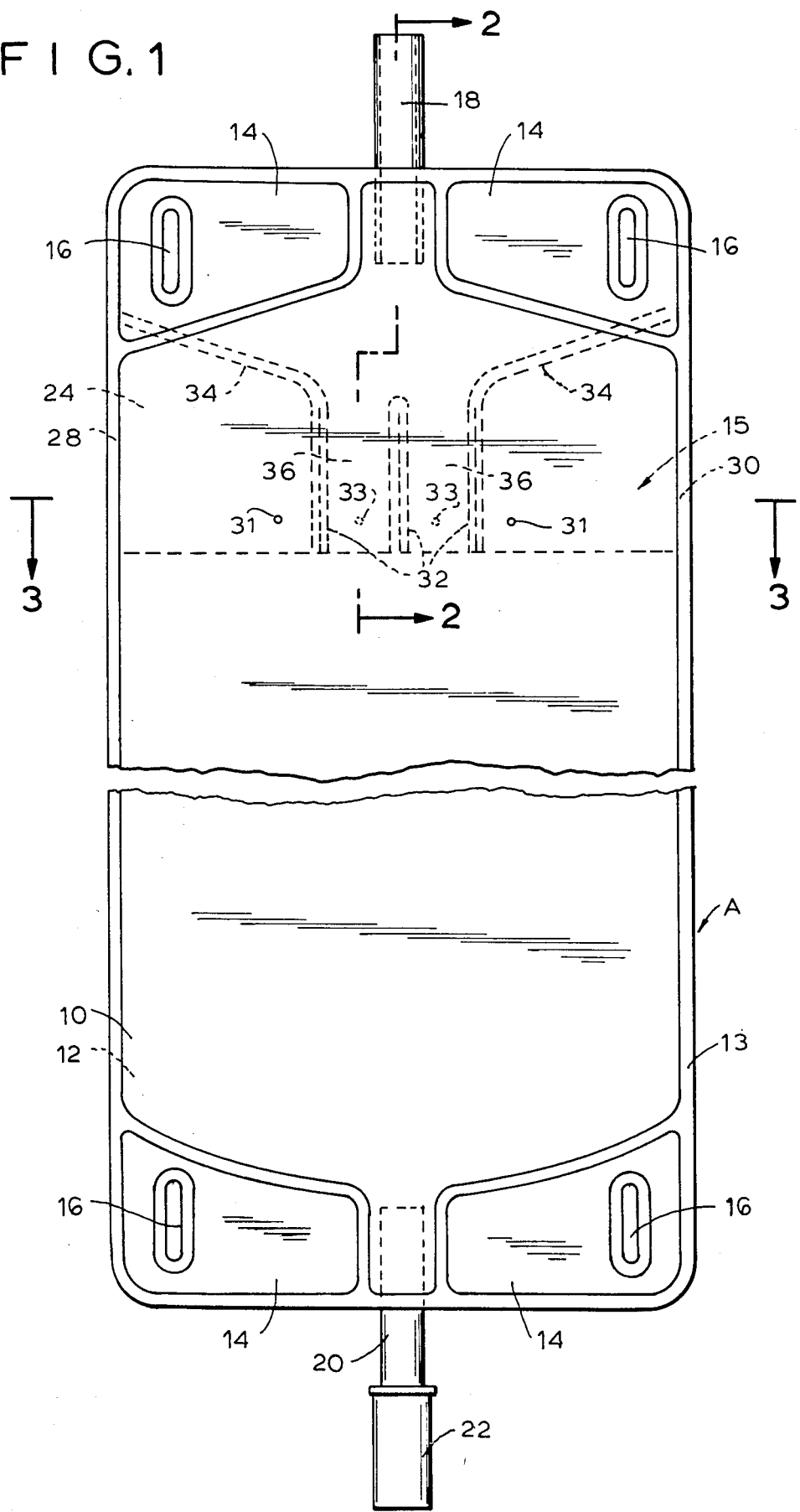
FIG. 1 is a front elevational view of a leg mountable urine collection receptacle including a first preferred embodiment of the present invention.

As seen in FIG. 1, the present invention relates to a non-return valve for use in a fluid collection receptacle adapted for medical purposes, for example, a urine drainage bag, generally designated A, designed for mounting to the leg of a mobile patient. Bag A comprises first and second generally rectangular walls 10, 12 of flexible plastic sealable material, preferably transparent or translucent. Walls 10 and 12 are elongated in the vertical direction. They are sealed together at the periphery 13 to form a fluid-tight reservoir body. Enlarged areas 14 at each of the corners of bag A are sealed in a conventional manner and provided with slots 16 through which mounting bands (not shown) preferably of elastic or the like may pass to permit bag A to be secured to the leg of the wearer.

At the top of bag A is provided a relatively rigid plastic inlet tube 18 designed to be connected to a flexible inlet tube (not shown). At the bottom of bag A is provided a relatively rigid outlet tube 20 with a conventional valve 22 slideably mounted thereon.

Situated between walls 10 and 12 is a drape 15 consisting of a pair of flexible sheets 24, 26 situated in side-by-side relation and preferably composed of the same or similar plastic material as walls 10 and 12. Drape 15 extends across the entire width of the bag body A and is generally rectangular in configuration. The side edges 28, 30 of drape 15 are substantially entirely sealed between opposing portions of the periphery 13 of walls 10, 12. Alternatively, one or more portions of drape 15 may also be welded to one or both of walls 10, 12, for example, by a spot weld as shown as 31 in FIG. 1.

Figure 11:
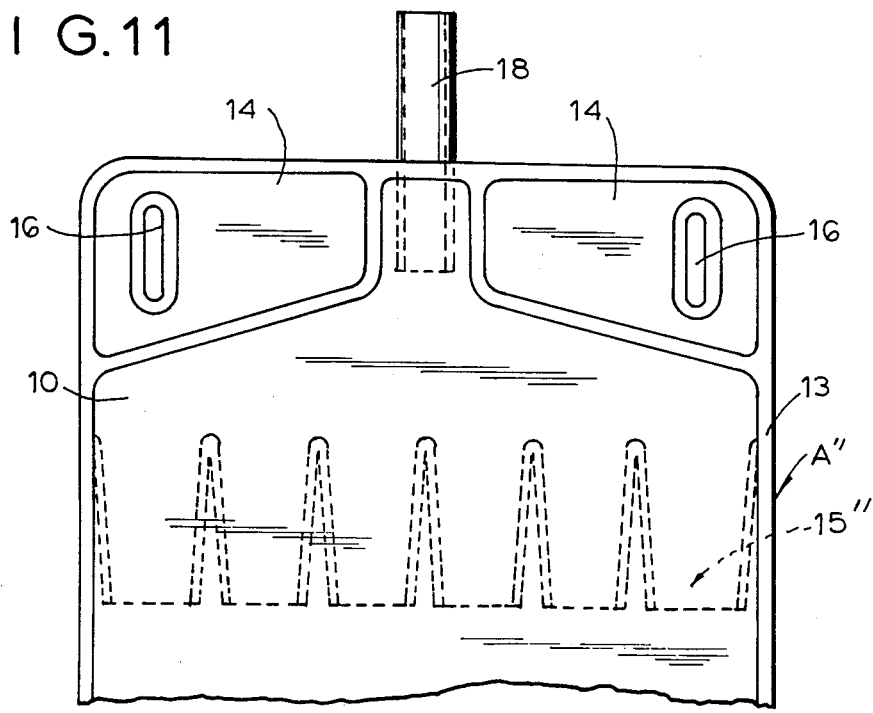
FIG. 11 is a fragmentary front elevational view of a third preferred embodiment of the present invention.

Sheets 24 and 26 are sealed together along spaced, substantially vertical line 32 (FIGS. 4 and 5) extending along the lower section of drape 15. The lower section of drape 15 extends from the bottom edge of the drape up to approximately the middle thereof. In addition, in all embodiments, except that shown in FIG. 11, sheets 24 and 26 are sealed together along lines 34 which extend in the upper section of drape 15 from side edges 28, 30 downwardly towards the lower section and inwardly toward the middle of the drape 15 and, therefore, towards vertical lines 32. Preferably, lines 34 and the outermost lines 32 are unitary, with a vertical section and an inclined section, for fabrication convenience.

Figure 2:
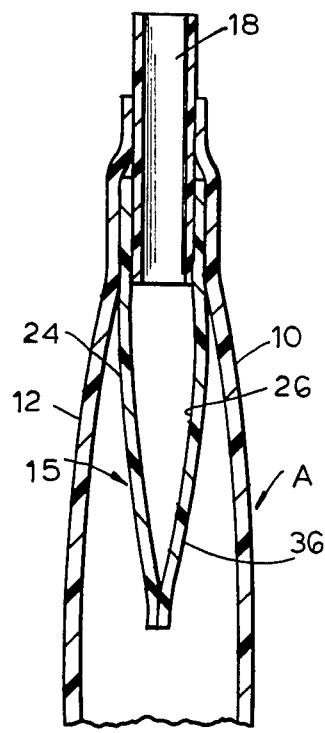
FIG. 2 is a fragmentary side cross-sectional view of a portion of the valve of the present invention taken along line 2—2 of FIG. 1.
Figure 3:
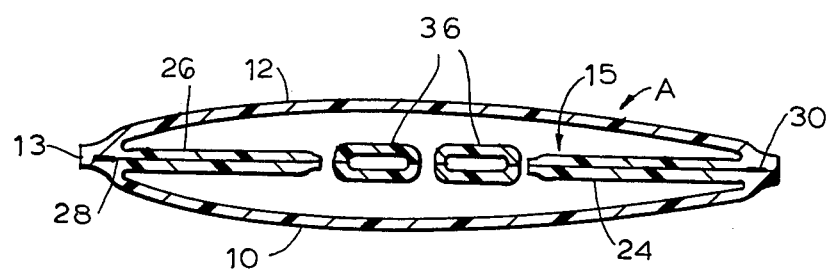
FIG. 3 is a top cross-sectional view of the receptacle of the present invention taken along line 3—3 of FIG. 1.

Drape 15 is severed along vertical lines 32 (FIGS. 6 and 7) such that adjacent pairs of vertical lines 32 define the bodies of flap valves 36 (FIG. 2). One, two, or multiple flap valves 36 may be provided, as desired. Lines 34 form a funnel-like structure above flap valves 36 such that any liquid passing through inlet tube 18 is funneled toward the middle of drape 15 and, hence, flap valves 36. In some cases it may be desirable to limit the width of the opening of flap valves 36 by means of a spot weld 33 or the like as shown in FIG. 1.

FIGS. 4-9 illustrate the process of fabricating the receptacle of the present invention. First, sheets 24 and 26 are sealed together along lines 32 and lines 34, if present, to form drape 15, as shown in FIG. 4. Sealing vertical lines 32 defines the bodies of flap valves 36 in the lower section of drape 15. Drape 15 may be as wide or wider than the eventual width of bag A and about as high as approximately one-quarter to one-third of the length of the bag. Drape 15 is then severed along lines 32 by cutting such that the bodies of the flap valves 36 are detached from the remainder of the drape. This permits the flap valves 36 to operate optimally. Valves 36 are formed at the bottom of the funnel-like structure defined by lines 34, as shown in FIG. 6.

Figure 8:
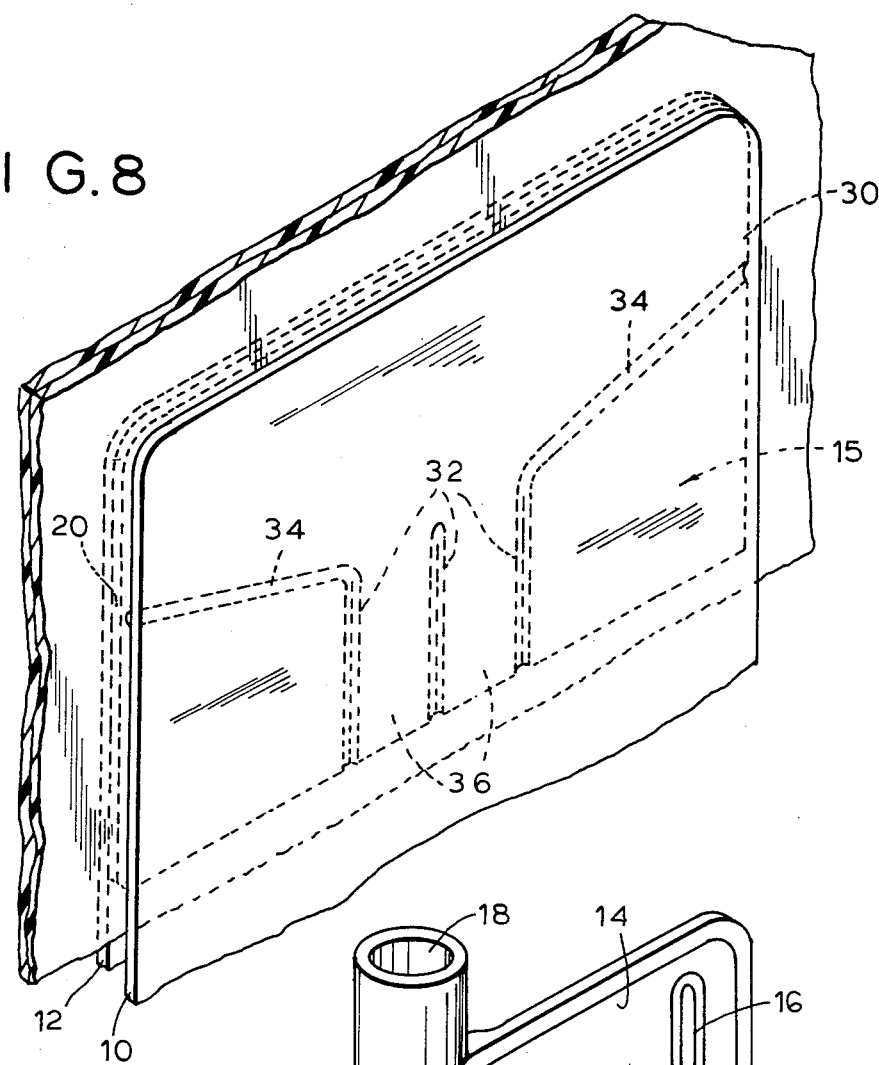
FIG. 8 is an isometric view of a portion of the receptacle of the present invention prior to sealing.
Figure 9:
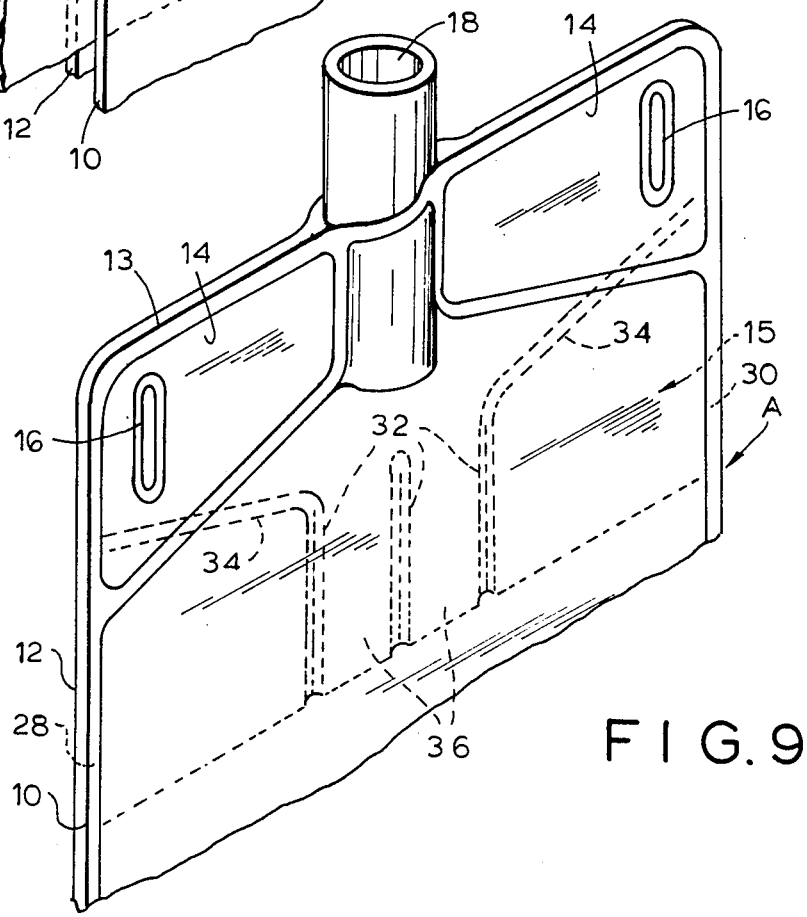
FIG. 9 is an isometric view of a portion of the receptacle of the present invention subsequent to sealing.
Figure 10:
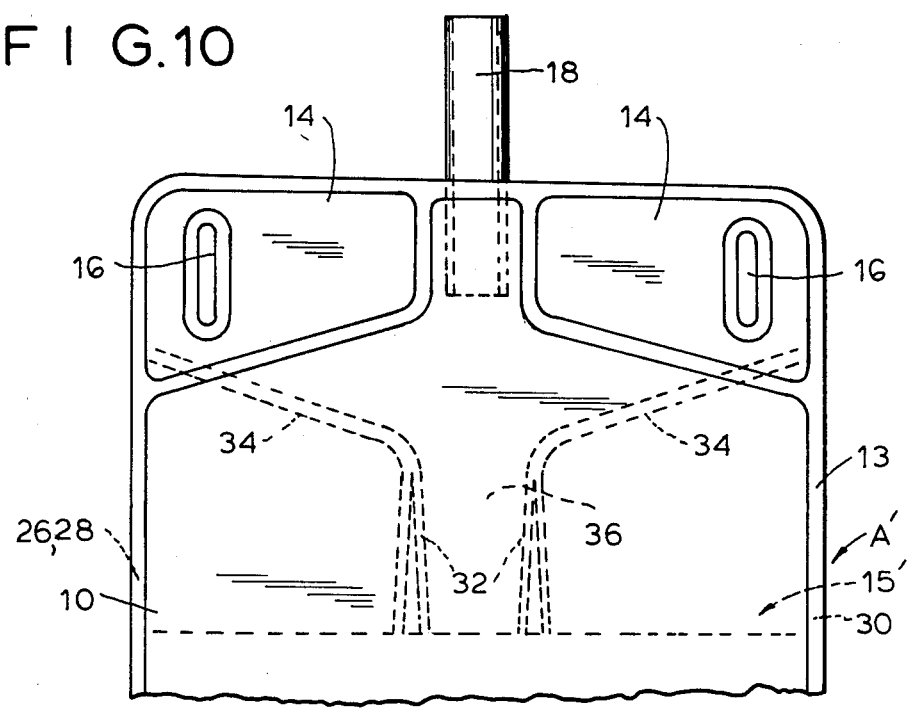
FIG. 10 is a fragmentary front elevational view of a second preferred embodiment of the present invention.

Drape 15 is then placed between walls 10 and 12 in the appropriate position, as seen in FIG. 8. The unit, along with an inlet tube 18 and an outlet tube 20, is passed through a conventional heat sealing or high frequency welding machine. The machine will seal the periphery 13 of the walls 10 and 12 to create the receptacle body with drape 15 therebetween such that side edges 28 and 30 of drape 15 are sealed along the periphery 13. Corner sections 14 are sealed at the same time. The body is then trimmed to remove the excess material.

It should now be appreciated that the non-return valve of the present invention can be fabricated using very simple and highly automated fabrication techniques. After the sheets 24 and 26 are sealed together to form the drape and severed along the appropriate sealed lines, the drape is simply inserted between the bag walls and the bag is sealed around the periphery in a single step sealing process.

While only a single preferred embodiment of the present invention has been disclosed herein for purposes of illustration, it is obvious that many variations and modifications could be made thereto. It is intended to cover all of these variations and modifications which fall within the scope of the present invention, as defined by the following claims:

I claim:

1. A fluid collection receptacle comprising a body formed of walls sealed along the periphery, a fluid inlet at the top of said body and a non-return valve within said body, said valve comprising first and second sheets, situated in substantially side by side relation, the sheets extending between the walls and across said body, at a point below said fluid inlet, with substantially the entire side edges of the sheets being sealed along substantially opposing sections to the wall periphery, said sheets being sealed to each other along spaced lines, said lines comprising generally parallel line sections, defining flap valve means, and generally inclined line sections, defining funnel means, said funnel means being situated between said fluid inlet and said flap valve means, said parallel line sections extending from the bottom edges of said sheets toward said inlet, said inclined line sections respectively extending from said flap valve means toward said opposing sections of the wall periphery, said sheets being detached along said parallel line sections to substantially separate said flap valve means from adjacent portions of said sheets.

2. The receptacle of claim 1 further comprising means for attaching each of said adjacent portions of said sheets to at least one of the walls proximate thereto.

3. The receptacle of claim 1, further comprising sets of spaced parallel line sections sealed and detached to define more than one flap valve means.

* * * * *